United States Patent [19]

Groger et al.

[11] Patent Number: 5,606,633
[45] Date of Patent: Feb. 25, 1997

[54] CHEMICAL DETECTOR EMPLOYING SURFACE PLASMON RESONANCE EXCITED USING AN OPTICAL WAVEGUIDE CONFIGURED AS AN ASYMMETRIC WAVEGUIDE COUPLER

[75] Inventors: Howard P. Groger, Gainesville; Martin Weiss, New Port Richey, both of Fla.; Peter Lo, Blacksburg; Bruce L. Thomas, Radford, both of Va.

[73] Assignee: American Research Corporation of Virginia, Radford, Va.

[21] Appl. No.: 495,764

[22] Filed: Jun. 26, 1995

[51] Int. Cl.$^6$ .................................................. G02B 6/10
[52] U.S. Cl. ............................ 385/12; 385/11; 385/131
[58] Field of Search .................................. 385/2, 11, 12, 385/13, 14, 31, 129, 130, 131, 132

[56] References Cited

U.S. PATENT DOCUMENTS

| | | | |
|---|---|---|---|
| 4,844,613 | 7/1989 | Batchelder et al. | 356/318 |
| 4,877,747 | 10/1989 | Stewart | 436/525 |
| 4,997,278 | 3/1991 | Finlan et al. | 356/128 |
| 5,023,053 | 6/1991 | Finlan | 422/82.05 |
| 5,035,863 | 7/1991 | Finlan et al. | 422/82.05 |
| 5,047,213 | 9/1991 | Finlan et al. | 422/82.11 |
| 5,055,265 | 10/1991 | Finlan | 422/82.05 |
| 5,067,788 | 11/1991 | Jannson et al. | 385/2 |
| 5,245,410 | 9/1993 | Villuendas Yuste et al. | 356/445 |
| 5,313,264 | 5/1994 | Ivarsson et al. | 356/73 |
| 5,322,798 | 6/1994 | Sadowski | 436/113 |
| 5,327,225 | 7/1994 | Bender et al. | 356/445 |
| 5,344,784 | 9/1994 | Attridge | 436/518 |
| 5,359,681 | 10/1994 | Jorgenson et al. | 385/12 |

*Primary Examiner*—John D. Lee
*Assistant Examiner*—Phan T. H. Palmer
*Attorney, Agent, or Firm*—James Creighton Wray

[57] ABSTRACT

A highly sensitive surface plasmon waveguide sensor monitors the refractive index and thickness of thin adsorbed films. The sensor includes an optical waveguide formed by ion-exchange in a glass substrate, by selective densification of substrate material or by the incorporation of high refractive index materials during deposition of a dielectric layer. Two dielectric thin films are deposited on top of the waveguide. The layer closest to the waveguide has a lower refractive index than the guiding layer to form a buffer layer. The second dielectric layer, or tuning layer, has a higher refractive index. The tuning and buffer layers allow optimization of the resonance wavelength, full-width half maximum of the resonance wavelength range and amplitude of the resonance. The tuning layer is coated with a thin metallic layer, to effect surface plasmon resonance, such as gold, silver, aluminum or one or more semiconducting materials. Alternatively the optical waveguide is coated with the buffer layer and the thin metal layer. The tuning layer and a second buffer layer are deposited on top of the metallic layer. Light is introduced to the waveguide and interaction between the light and the thin metal layer results in attenuation of the TM polarization. The ratio of the TM and TE polarization intensities is monitored by a polarization beam splitter. The relatively unchanged TE polarization intensity serves as an integral reference for the sensor. The sensor has numerous applications in the environmental and biomedical fields.

28 Claims, 8 Drawing Sheets

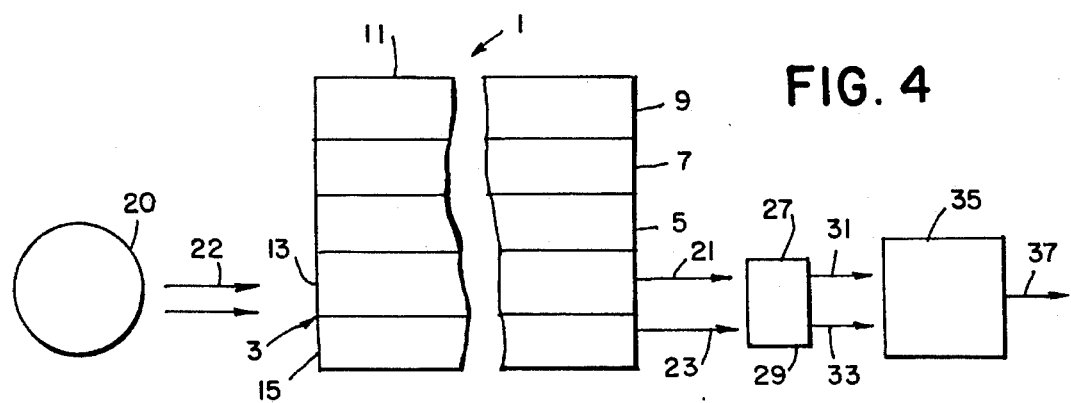
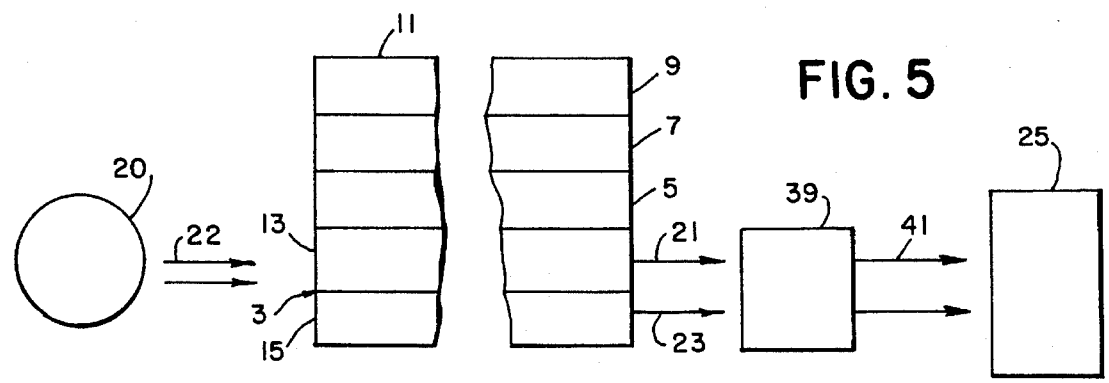
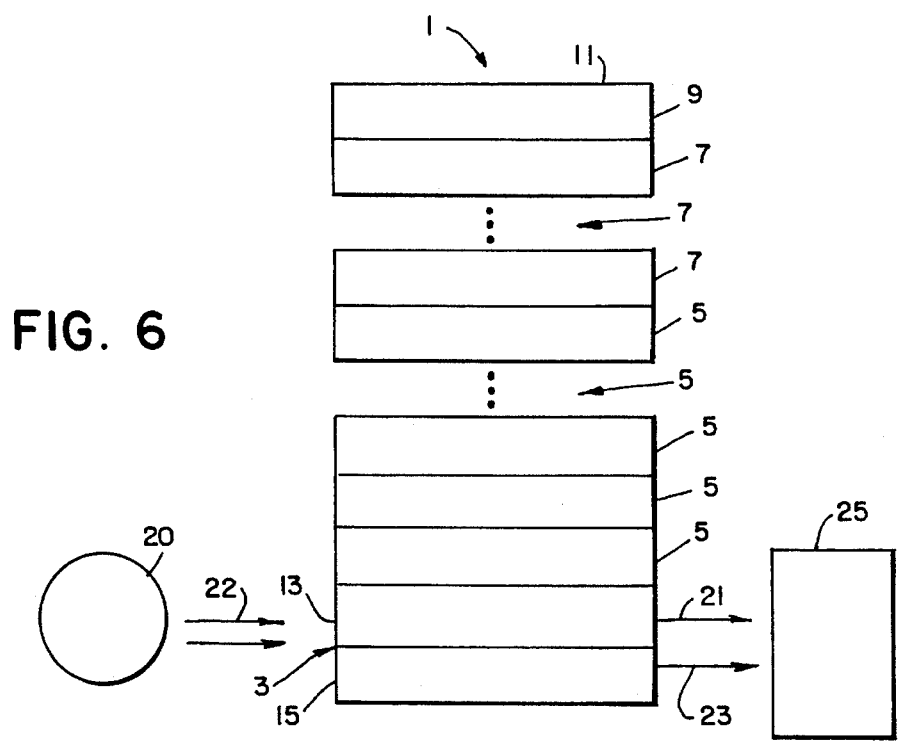

CHEMICAL DETECTOR EMPLOYING SURFACE PLASMON RESONANCE EXCITED USING AN OPTICAL WAVEGUIDE CONFIGURED AS AN ASYMMETRIC WAVEGUIDE COUPLER

BACKGROUND OF THE INVENTION

This invention relates to chemical sensors based on surface plasmon resonance.

Optical surface plasmon devices are effective chemical detectors because of the extreme sensitivity of the plasmon resonance to environmental changes. Surface plasmon devices are used in numerous sensing applications including pollution monitoring, toxic gas detection, biochemical measurements and biomedical monitoring. Surface plasmon resonance sensors respond to changes in refractive index or thickness of films adsorbed to the sensing layer and are of particular interest in detecting immunological reactions. Besides sensor applications, the surface plasmon devices have also proven effective as polarizers and as polarization splitters.

A surface plasmon wave is a lossy TM-polarized electromagnetic wave supported by a metal-dielectric interface. When the metal has a finite thickness, individual surface plasmons are supported on both sides of the metal. Further, if the metal is sufficiently thin, such as on the order of the penetration depth of the optical wave, the two surface plasmons are coupled, forming the symmetric and antisymmetric bound and leaky modes.

Existing surface plasmon sensors are classical attenuated total reflection devices. Excitation of the surface plasmon modes is monitored by measuring reflected power as a function of angle. However, those sensors may be costly, are difficult to use for simultaneous multiple analytical evaluations, are not amenable to chemical analysis in restricted geometries and are difficult to apply in remote sensing.

Recently, efforts have shifted toward designing surface plasmon sensors based on optical waveguides coated with thin metallic layers. In those configurations, analyte detection is afforded by monitoring the ratio of the TM and TE modal insertion losses. That ratio is referred to as the extinction ratio. Surface plasmon waves are excited by TM-polarized waveguide modes. Excitation occurs when the surface plasmon waves and the TM waveguide modes are phase matched, resulting in a coupled wave system. The resulting normal modes have complex propagation constants, owing to the loss induced by the surface plasmon. TE-polarized waveguide modes do not interact with the surface plasmons and experience a small, relatively constant loss due to the presence of the metal layer. Effectively, in the TM polarization, the metal-clad waveguide functions as an asymmetric directional coupler in which a first arm is the metal layer supporting the plasmon modes and a second arm is the dielectric waveguide. Surface plasmon excitation is strongly dependent on wavelength. When the surface plasmon mode and the waveguide mode are phase-matched, the resulting TM normal mode propagates with high loss. When the two modes are not phase-matched, propagation loss is considerably lower. Typically, a thin dielectric buffer layer is inserted between the waveguide and the metal layer to control insertion losses. In most surface plasmon waveguide designs, that buffer layer is very thin, giving rise to strong coupling between the surface plasmons and the waveguide modes. That strong coupling makes analysis by traditional coupled mode techniques inappropriate. Additionally, the thicknesses of both the metal layers and the buffer layers in existing sensors must be adjusted to allow plasmon resonance to occur at the proper excitation wavelength. That complicates the design process.

Needs exist for highly sensitive surface plasmon waveguide sensors that are precise, efficient, suitable for diverse sensing applications and capable of remote operation.

SUMMARY OF THE INVENTION

This invention provides a highly sensitive surface plasmon waveguide sensor that simultaneously responds to both the thickness and the refractive index of an adsorbed layer by measuring the extinction ratio at two wavelengths.

The sensor includes an optical waveguide structure formed by depositing a material having a high refractive index on a substrate having a low refractive index or by forming a region having a high refractive index by ion exchange, laser densification or other process. The sensor includes an optical waveguide formed by ion-exchange in a glass substrate, selective densification of a substrate material or incorporation of high refractive index materials during deposition of a dielectric layer. Two dielectric thin films are deposited on top of the waveguide. The layer closest to the waveguide has a lower refractive index than the guiding layer of the waveguide and is called the buffer layer. The second dielectric layer has a higher refractive index than the buffer layer and is called the tuning layer. The tuning and buffer layers allow optimization of the resonance wavelength, full-width half maximum of the resonance wavelength range and amplitude of the resonance. The tuning layer is coated with a thin metallic layer known to cause surface plasmon resonance comprised of metals such as gold, silver, aluminum or one or more semiconducting materials. Alternatively, the optical waveguide is coated with the buffer layer and thin metallic layer. The tuning layer and a second buffer layer are deposited on top of the metallic layer.

Light is introduced to the waveguide and interaction between the light and the thin metal layer results in attenuation of the transverse magnetic (TM) polarized propagating mode. The ratio of the TM and the transverse electric (TE) polarization intensities is monitored using a polarization beam splitter. The relatively unchanged TE polarization intensity serves as an integral reference for the sensor.

The sensor is sensitive to both the refractive index and the thickness of the adsorbed film. Inserting the high refractive index dielectric layer between the metal and buffer layers allows for considerable tuning of the plasmon resonance. When coated with a thin layer of moisture-sensitive polymer such as Nafion fluoropolymer, the surface plasmon waveguide operates as a humidity sensor.

The present invention can detect changes in refractive index to 1 ppm at a measurement precision of 2%. Additionally, the sensor can measure changes in the thickness of an adsorbed film in the range of 2 nm to 0.7 microns. In particular, a waveguide configuration described below has sensitivity to small changes in adsorbed film thickness sufficient to measure antibody-antigen binding for immunoassay or to measure other receptor/analyte interactions. The configuration is as follows:

50 nm silicon dioxide 50 nm Tantalum Pentoxide 25 nm gold 1 micron silicon dioxide Potassium ion exchanged waveguide in BK7 glass The waveguide geometry of the present invention allows surface plasmon sensors to be incorporated in integrated optical systems, thereby creating the potential for devices having multianalyte sensing capability and built-in signal processing. As an example, a sensor for analyzing multiple samples using immunological methods is prepared by patterning a multiplicity of surface plasmon waveguides on a substrate and covering the waveguides with a plate such that fluid deposited on the top of the plate interacts with one or more waveguides. Integrated polarization beam splitters allow the TE and the TM channels from each waveguide to be separated and light traveling in the TE and TM channels is detected using a charge coupled device camera.

The present invention, unlike existing surface plasmon waveguide sensors, has a tuning layer. Tuning the spectral response of asymmetric Y-branches and directional couplers is accomplished by inserting a thin, high refractive index tuning layer between the metal and buffer layers of the sensor. That tuning layer preferentially affects the propagation constant of one of the arms, thereby shifting the phase-matched wavelength. The thickness of the tuning layer primarily affects only the plasmon propagation constants, thereby allowing significant tuning of the spectral response to be realized. In existing sensors, the thicknesses of both the metal layers and the buffer layers must be adjusted to allow plasmon resonance to occur at the proper excitation wavelength. The present invention simplifies the process by allowing resonance wavelength to be controlled predominantly by the thickness of the tuning layer and allows effective tuning of plasmon response to be achieved.

These and further and other objects and features of the invention are apparent in the disclosure, which includes the above and ongoing written specification, with the claims and the drawings.

BRIEF DESCRIPTION OF THE DRAWINGS

FIG. 4 is a schematically shows the present invention having a detector that includes a pair of photodiodes and an amplifier.

FIG. 5 schematically shows an embodiment of the present invention having a modulator for receiving and modulating the TE and TM signals.

FIG. 6 schematically shows an embodiment of the present invention having multiple buffer and tuning layers.

DETAILED DESCRIPTION OF THE PREFERRED EMBODIMENTS

Figure 1:
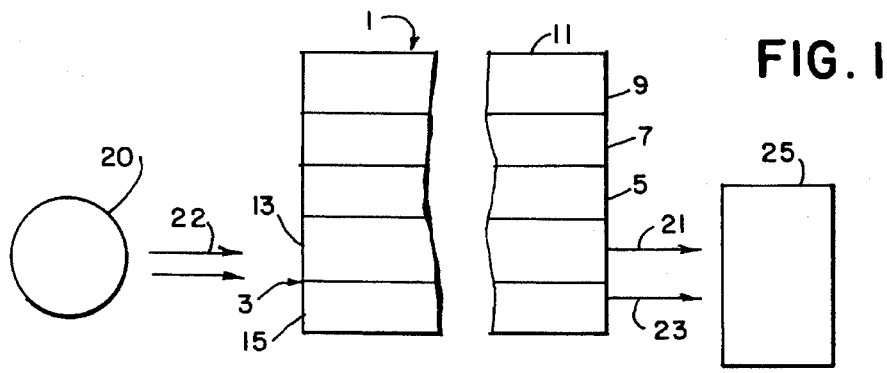
FIG. 1 is a schematic side view of the present invention having a light source, a detector and a surface plasmon resonance waveguide sensor. The sensor includes an optical waveguide structure, a buffer layer, a tuning layer and a metal layer.
Figure 2:
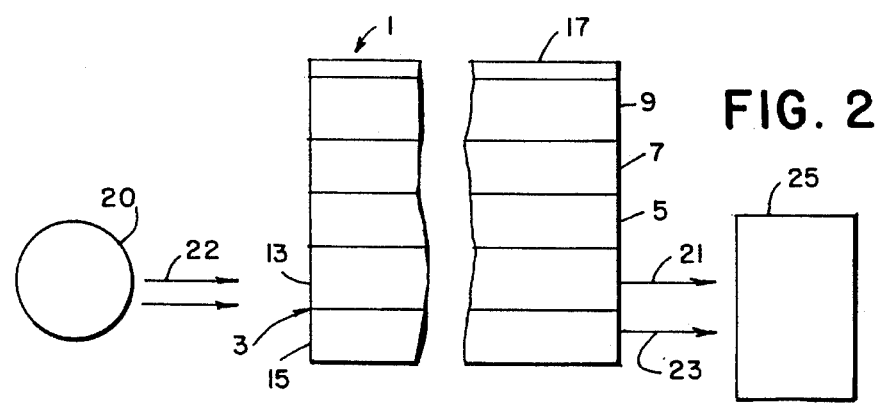
FIG. 2 is a schematic side view of a surface plasmon resonance waveguide sensor having an optical waveguide structure, a buffer layer, a tuning layer, a metal layer and a thin coating layer over the metal layer.

Referring to FIG. 1, a surface plasmon sensor 1 includes an optical waveguide structure 3, a buffer layer 5, a tuning layer 7 and a thin metal layer 9. The active region 11 of the sensor 1 is the outer surface of the metal layer. Chemical or biological agents to be sensed come interact with the active region 11 of the metal layer 9. The optical waveguide 3 is formed by depositing a material 13 having a high refractive index on a substrate 15 having a low refractive index. In one preferred embodiment, BK-7 glass is deposited on soda-lime glass. The refractive index of BK-7 glass is 1.5155 at 0.63 micron wavelength excitation, and the refractive index of soda-lime glass at the same excitation wavelength is 1.510. Other combinations of materials that can be used to form the optical waveguide structure 3 include, but are not limited to, ion-exchanged potassium in BK-7 glass, polyimide deposited on soda-lime glass, poly(methyl methacrylate) on a fused silica or on silica sol-gel, and alumina deposited on soda-lime glass.

The buffer layer 5 overlies the optical waveguide structure 3 and is made of a low refractive index material. The tuning layer 7 overlies the buffer layer 5 and is made of a high refractive index material. The thin metallic layer 9 covers the entire assembly.

In a preferred embodiment, the optical waveguide structure 3 includes a potassium ion-exchanged soda-lime glass 13 deposited on a soda-lime glass substrate 15. The buffer layer 5 is a silicon dioxide layer; the tuning layer 7 is a titanium oxide layer and the metal layer 9 is a gold layer. Preferably, the silicon dioxide layer is 0.5 micron thick, the titanium oxide layer is 0.055 micron thick, and the gold layer is 0.030 micron thick.

Another preferred embodiment includes a potassium ion-exchanged waveguide having an exchange depth of three microns coated with a silicon dioxide buffer layer of 0.4 micron and a silicon nitride tuning layer of 0.125 micron. A 0.03 micron thick layer of gold is deposited over the coated waveguide structure. Decreasing the buffer layer thickness to 0.3 microns results in a sensor having a higher extinction ratio at resonance with TE propagation losses on the order of 10 dB/cm.

As shown in FIG. 1, the chemical sensor 1 detects surface plasmon resonance based on changes in the polarization extinction ratio. A light source 20 emits light 22 towards the optical waveguide structure 3 of the sensor 1. Light propagating through the optical waveguide structure 3 is affected by the presence of a thin metallic layer 9 deposited above the buffer layer 5 and the tuning layer 7 on the waveguide 3. The metallic layer 9 causes the attenuation of the TM polarization. TE signals 21 and TM signals 23 exit the waveguide 3 of sensor 1. The ratio of TE and TM polarization intensities is monitored using a detector 25, which may include a bulk polarization beam splitter or a waveguide polarization beam splitter. In evaluating the polarization extinction ratio, the unchanged TE polarization intensity serves as a reference signal for the sensor 1.

Figure 3:
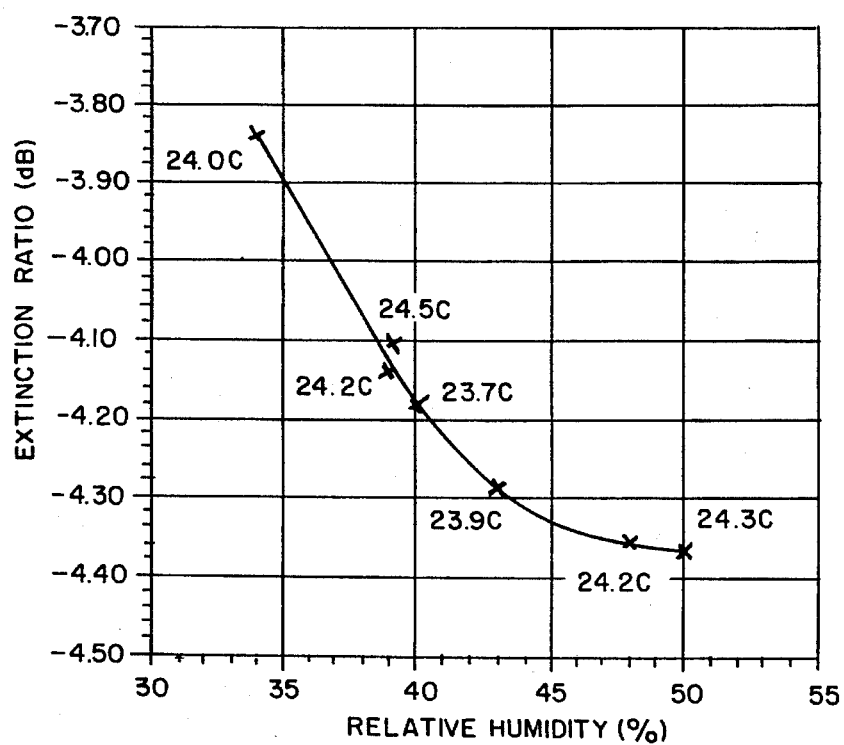
FIG. 3 is a graphically shows the measured humidity response of a nafion-coated surface plasmon waveguide sensor using an excitation wavelength of 632.8 nm.

In another preferred embodiment the coating layer 17 is a copper phtalocyanine layer. That creates a sensor where the adsorption, and hence the refractive indexes, of the layers would be a function of nitrous oxide. In another preferred embodiment, the coating layer 17 is a thin nafion fluoropolymer layer. Having that layer, the sensor 1 functions as a humidity sensor. FIG. 3 graphically shows the measured humidity response of a nafion-coated surface plasmon waveguide sensor.

In a preferred embodiment of the sensor as shown in FIG. 4, the difference between TE signal 21 and TM signal 23 polarization intensities is detected by feeding TE output intensity 21 to one photodiode 27 and TM output intensity 23 to a second photodiode 29. The outputs 31, 33 of both photodiodes 27, 29 are routed to a lock-in amplifier 35 to provide a difference signal 37. Normalization of the difference signal 37 by division of the TE polarization signal 21 provides a precise measurement of the change in surface plasmon resonance response.

As shown in FIG. 5, a modulator 39 can be incorporated in the embodiment shown in FIG. 1. The modulator 39 modulates the TE signals 21 and the TM signals 23 and delivers modulated signals 41 to the detector 25. In a preferred embodiment, the modulator 39 is an electro-optic modulator that allows for synchronous detection of the polarization extinction ratio. Other signal modulator means, such as vibrating mirrors and electrically controlled Mach-Zehnder interferometers, can be used to increase signal precision and to decrease the limit of detectability for a range of analytes.

Preferred embodiments of the present invention have both buffer layers 5 and tuning layers 7. The thickness and refractive index distributions of the buffer layers 5 and the tuning layers 7 are selected to provide optimal response. As shown in FIG. 6, the sensor 1 can have multiple buffer layers 5 and multiple tuning layers 7. Multiple buffer layers 5 and multiple tuning layers 7 optimize the slope of the dependence of polarization extinction ratio on the refractive index of the analyte.

A wide range of reagents can be used to provide a sensitive method for detecting analytes. In one embodiment, an antibody is coupled to a gold surface. The presence of the matched antigen results in the formation of an antibody/antigen complex. The formation of the complex produces a change in the refractive index of the material in contact with the gold layer. That effect is detectable as a change in polarization extinction ratio or a change in the wavelength distribution of the light transmitted by the waveguide.

A preferred configuration of the present invention is as follows:

50 nm silicon dioxide 50 nm Tantalum Pentoxide 25 nm gold 1 micron silicon dioxide Potassium ion exchanged waveguide in BK7 glass A wide variety of other coating types and thicknesses may be used to improve the use of the surface plasmon waveguide sensor with immunoassay test materials.

In a similar embodiment, the surface plasmon sensor is used to detect the presence of micro-organisms either through an immunochemical effect or through the use of an affinity surface. In one example, the surface plasmon waveguide structure is modified by carboxylated dextran to adsorb micro-organisms. When the surface plasmon waveguide structure is introduced to a solution containing micro-organisms, the surface plasmon resonance output is a function of the concentration of micro-organisms present.

In a third embodiment, a sensor for high molecular weight materials is created by coupling a glycoconjugate material to the gold layer of the surface plasmon waveguide. That sensor is effective in detecting toxins.

In a fourth embodiment, the thickness and refractive index distributions of the buffer and tuning layers are selected to provide optimal response to vapor phase analytes.

Figure 7:
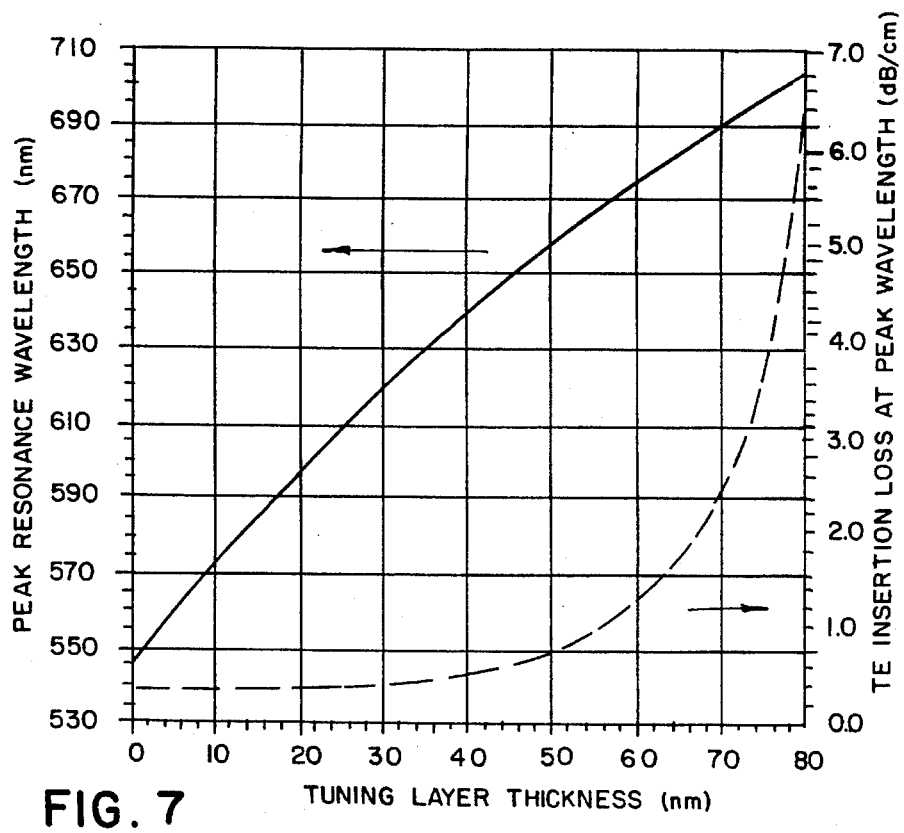
FIG. 7 graphically illustrates peak resonance wavelength and TE insertion loss at resonance as functions of tuning layer thickness.

The resonance characteristics of the surface plasmon waveguide sensor make the device extremely sensitive to parameter variations. FIG. 7 shows effects on peak resonance wavelength and TE insertion losses resulting from varying the thickness of the tuning layer. The superstrate refractive index is assumed to be 1.415. Peak resonance wavelength can be varied continuously over almost 100 nm without adversely affecting the TE insertion losses, simply by changing the thickness of the tuning layer. The polarization extinction ratio is generally constant over that range as well. Any TE losses can be reduced by using a thicker tuning layer having a slightly lower refractive index.

Figure 8:
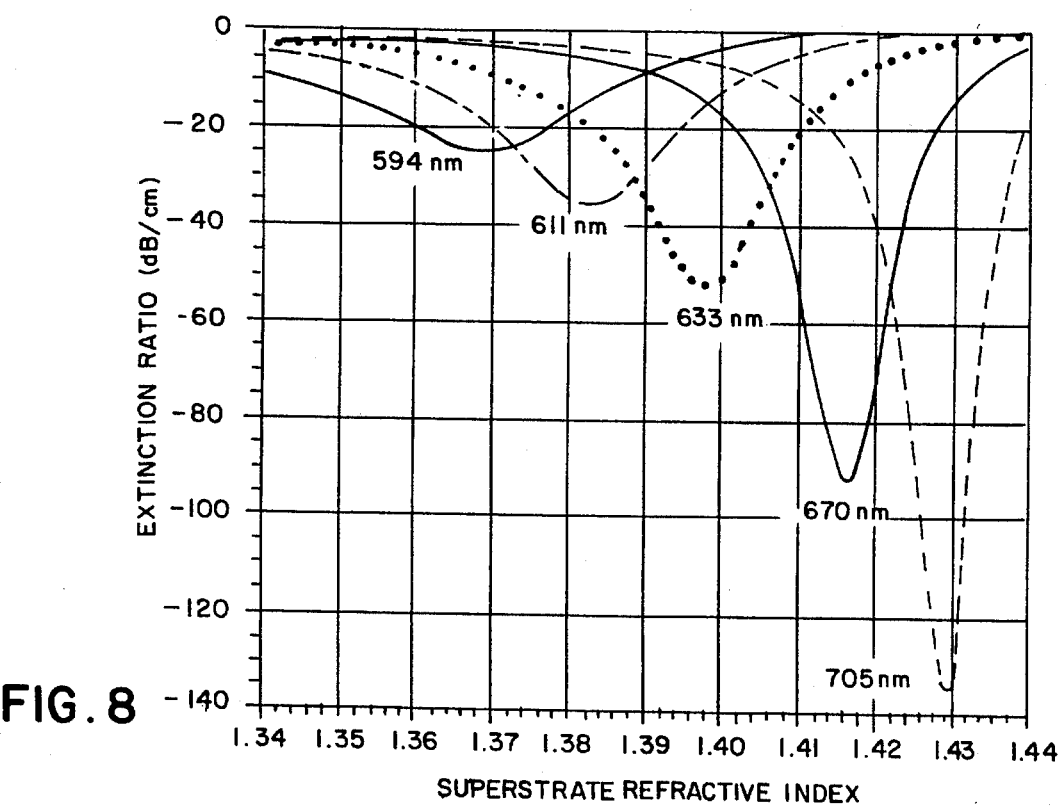
FIG. 8 graphically illustrates extinction ratio versus surface active region index for several different excitation wavelengths.

Peak resonance wavelength is also a function of the superstrate refractive index. Resizing the tuning layer thickness effectively changes the superstrate refractive index value about which the sensor is biased for a given wavelength. A shown in FIG. 8, when the tuning layer thickness is decreased, the extinction ratio curves are shifted to peak at lower cover region refractive index values. Thus, by simply changing the thickness of the tuning layer, the sensor can be used to detect refractive index changes over a wide range.

Figure 9:
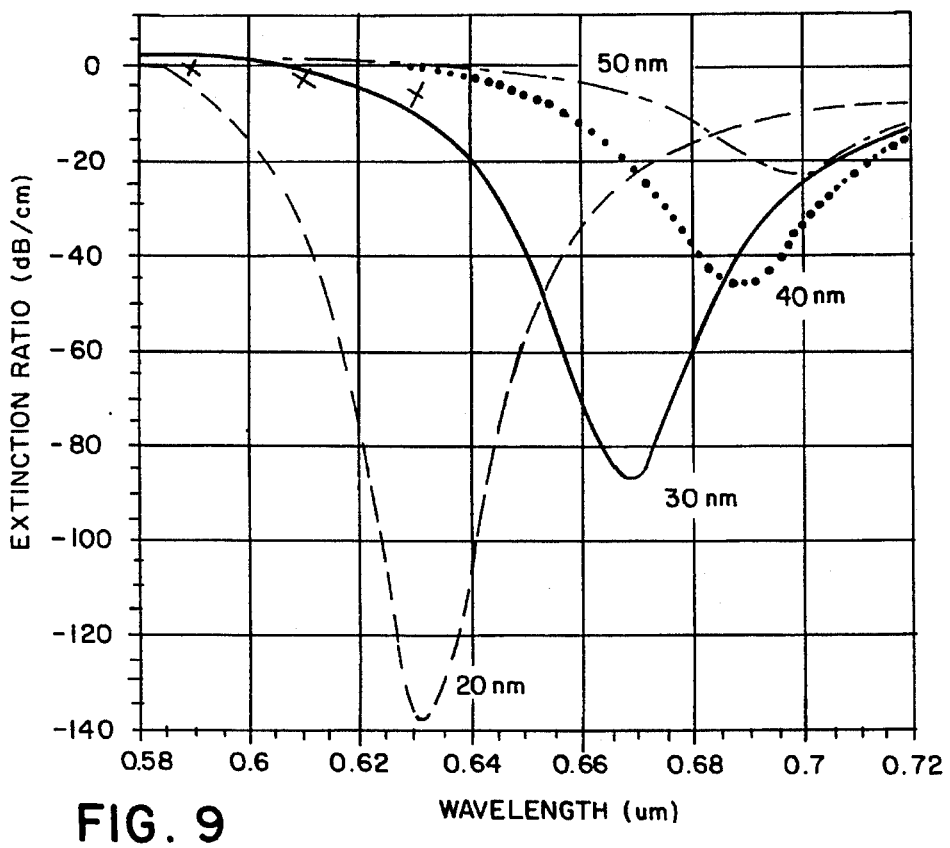
FIG. 9 graphically illustrates extinction ratio as a function of wavelength for several different metal layer thicknesses.

The thickness of the metal layer is important in determining the characteristics of the surface plasmons which the layer supports. The metal layer needs to be adequately thin, such that individual plasmons guided at the air and at the tuning layer interfaces remain coupled. That ensures a high level of sensitivity to the levels of foreign materials in the superstrate. However, as the gold layer becomes thicker, the change in surface plasmon mode indices with gold thickness becomes more gradual which allows the center wavelength of the resonance to be controlled by the thickness of the tuning layer. FIG. 9 graphically shows the extinction ratio as a function of wavelength for different metal layer thicknesses.

Figure 10:
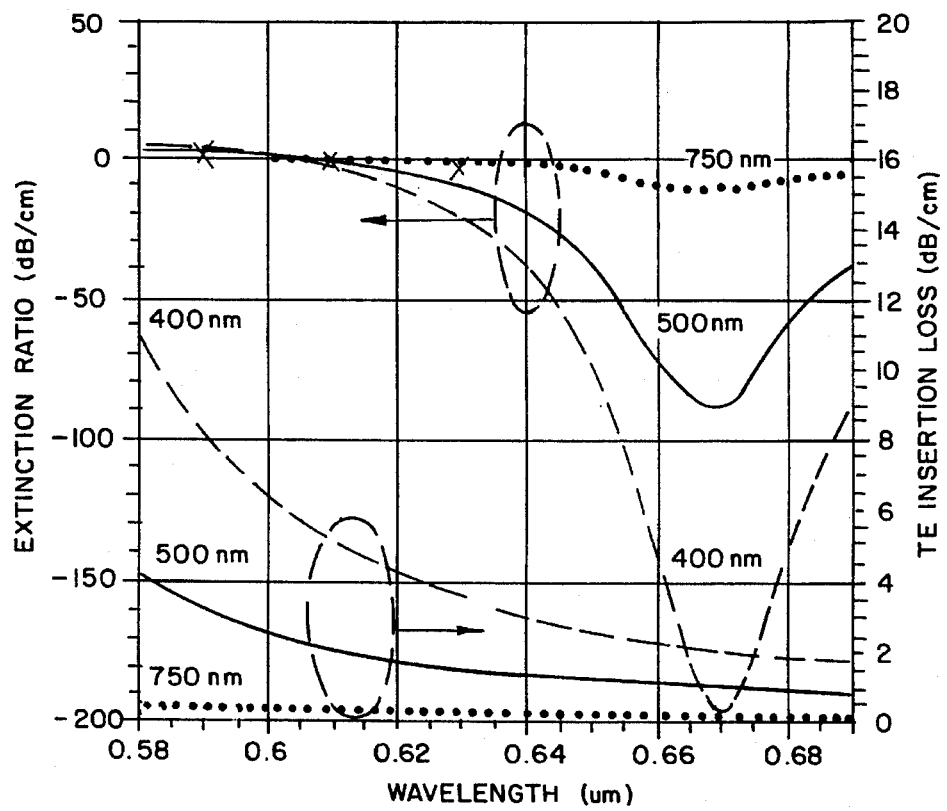
FIG. 10 graphically illustrates extinction ratio as a function of wavelength for several different buffer layer thicknesses.

The thickness of the buffer layer controls the maximum extinction ratio and the TE insertion loss. Changing the buffer layer thickness modifies the strength of coupling between the surface plasmon mode and the TM-polarized waveguide mode. Because of differences in modal confinement and dispersion, different excitation wavelengths effectively experience different buffer layer thicknesses. Decreasing buffer layer thickness increases the excitation ratio but also leads to increased TE insertion losses. To a lesser extent, the thickness of a buffer layer affects peak resonance wavelength. FIG. 10 graphically shows the extinction ratio as a function of wavelength for different buffer layer thicknesses.

Figure 11:
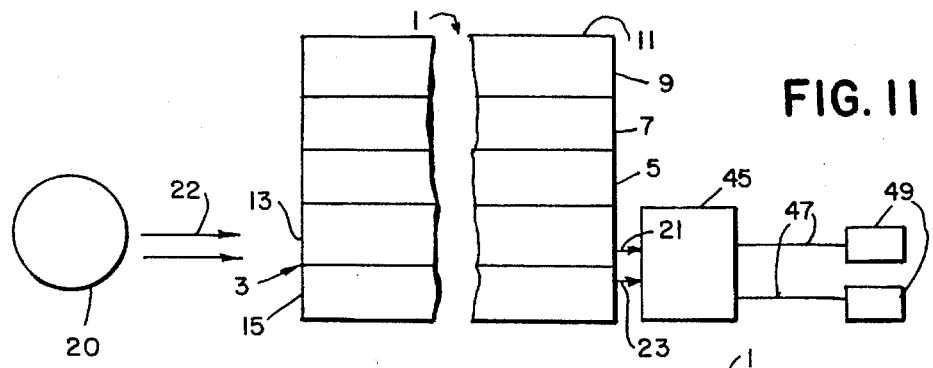
FIG. 11 schematically shows an integrated optic polarization beam splitter in series with the surface plasmon sensor and coupling each output to independent photodetectors.

When buffer layers are made thin enough to allow excitation ratios of several hundred dB/cm to be attained, noise arising from factors such as laser power fluctuations and manual polarizer alignment may significantly degrade the reproducibility of measurements. As shown in FIG. 11, some of that noise can be suppressed by incorporating an integrated optic polarization beam splitter 45 in series with the surface plasmon sensor 1 and coupling each output 47 to independent photodetectors 49. Inclusion of the integrated optic polarization beam splitter 45 in the design improves measurement accuracy and should allow the sensor 1 to detect refractive index changes in the ppm range.

In preferred embodiments, the planar waveguide is formed in a glass substrate through an ion-exchange process. A substrate is cleaned and placed in a pure bath, such as a pure $KNO_3$ bath, to create a waveguide. In a preferred embodiment, the substrate is placed in a pure $KNO_3$ bath at 375° C. for 3.5 hours, thereby forming a 3 μm deep planar waveguide. The waveguide is subsequently cleaned. A buffer layer, a tuning layer and a metal layer are sequentially deposited on the waveguide. In preferred embodiments, the layers are deposited using an electron-beam evaporator. The end faces of the sensor are polished using conventional techniques.

Figure 12:
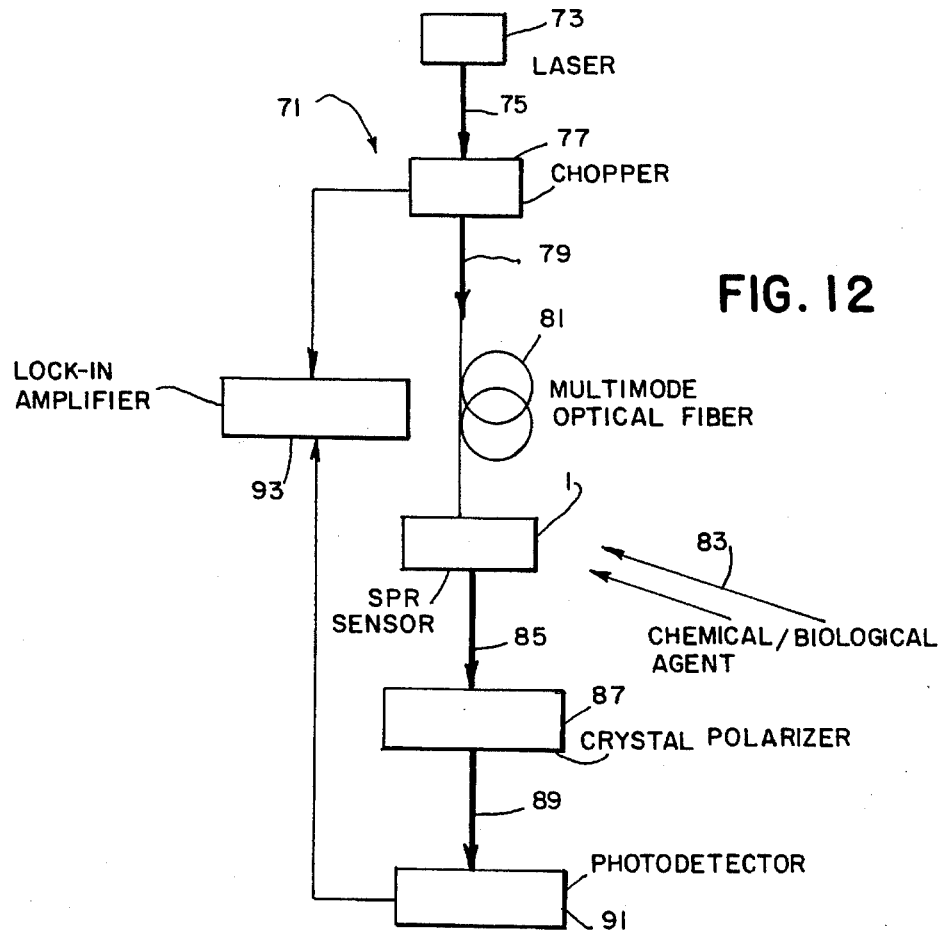
FIG. 12 shows a detection system having a light source, a chopper, an optical fiber, a surface plasmon resonance waveguide sensor, a polarizer, a photodetector and a lock-in amplifier.

FIG. 12 shows a detection system 71 that includes the surface plasmon waveguide sensor 1. A light source 73, such as a laser, delivers light signals 75 to a chopper 77. The chopper 77 interrupts the light signals 75 and delivers interrupted light signals 79 through an optical fiber 81 to the sensor 1. Chemical or biological analytes 83 in the vicinity of the sensor 1 are adsorbed as a thin film onto the sensor 1, thereby effecting the light as is travels through the optical waveguide of the sensor 1. Light output 85 of the sensor 1 is delivered to a polarizer 87, such as a crystal polarizer. The polarizer 87 delivers polarized signals 89 to a photodetector 91. In preferred embodiments, the photodetector 91 is connected to a lock-in amplifier 93. The refractive indexes and thicknesses of the film with the chemical or biological agent adsorbed on the sensor are subsequently determined.

Figure 13:
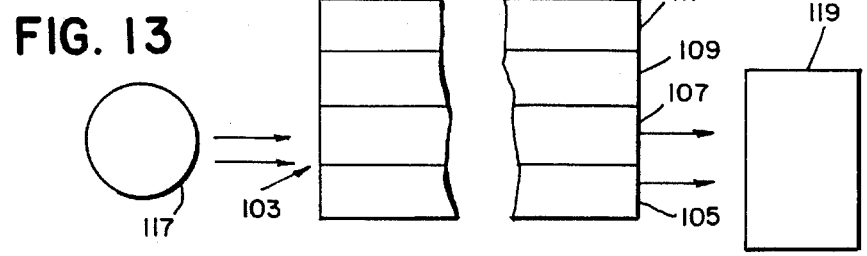
FIG. 13 is a schematic side view of an embodiment of the present invention having a light source, a detector and a surface plasmon resonance waveguide sensor. The sensor includes an optical waveguide structure, a first buffer layer, a tuning layer, a metal layer and a second buffer layer.
Figure 14:
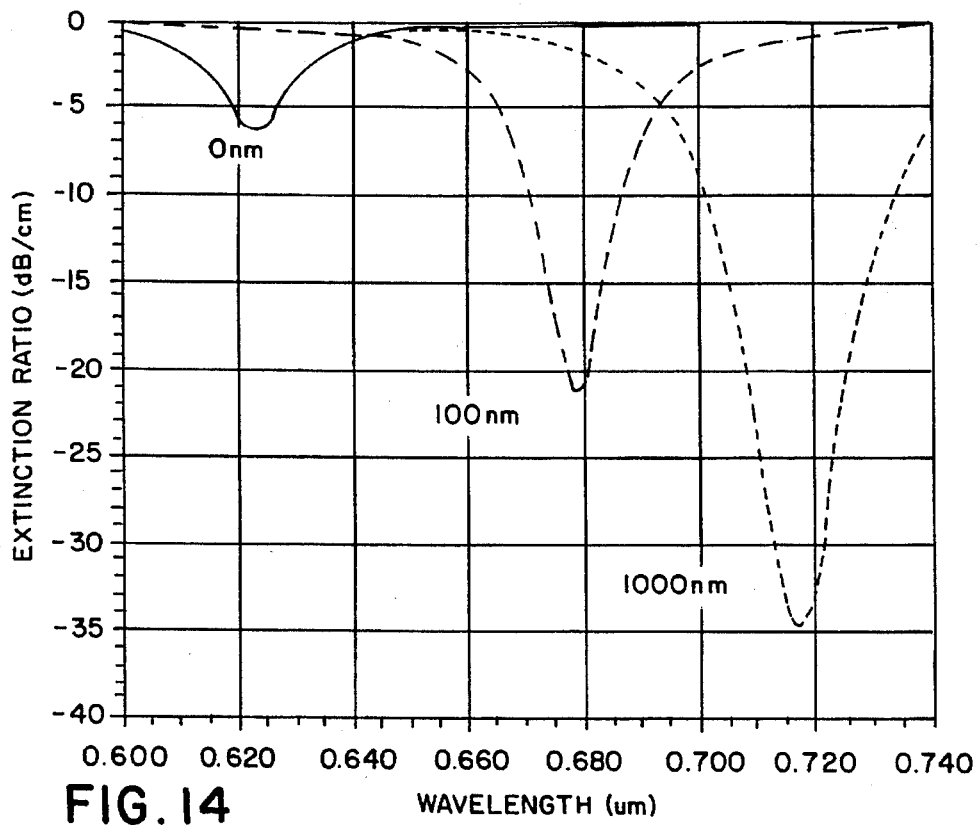
FIG. 14 graphically illustrates extinction ratio as a function of wavelength for several different metal layer thicknesses for the sensor shown in FIG. 13.
Figure 15:
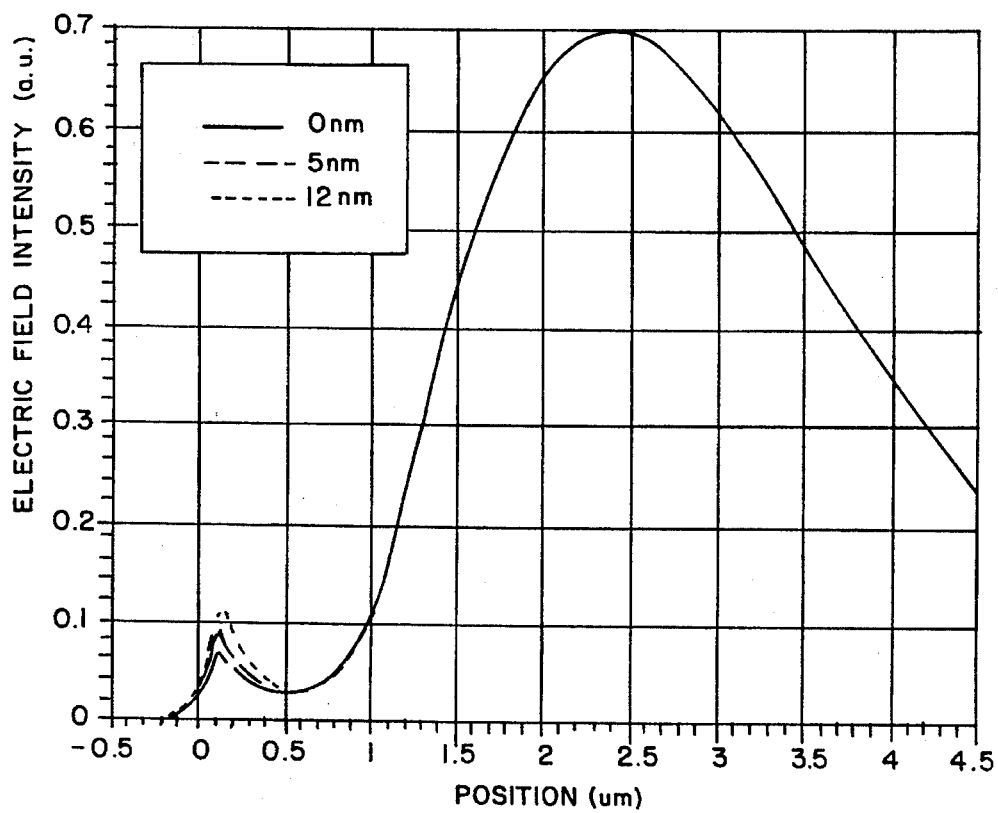
FIG. 15 graphically illustrates electric field intensity as a function of position for the sensor shown in FIG. 13.
Figure 16:
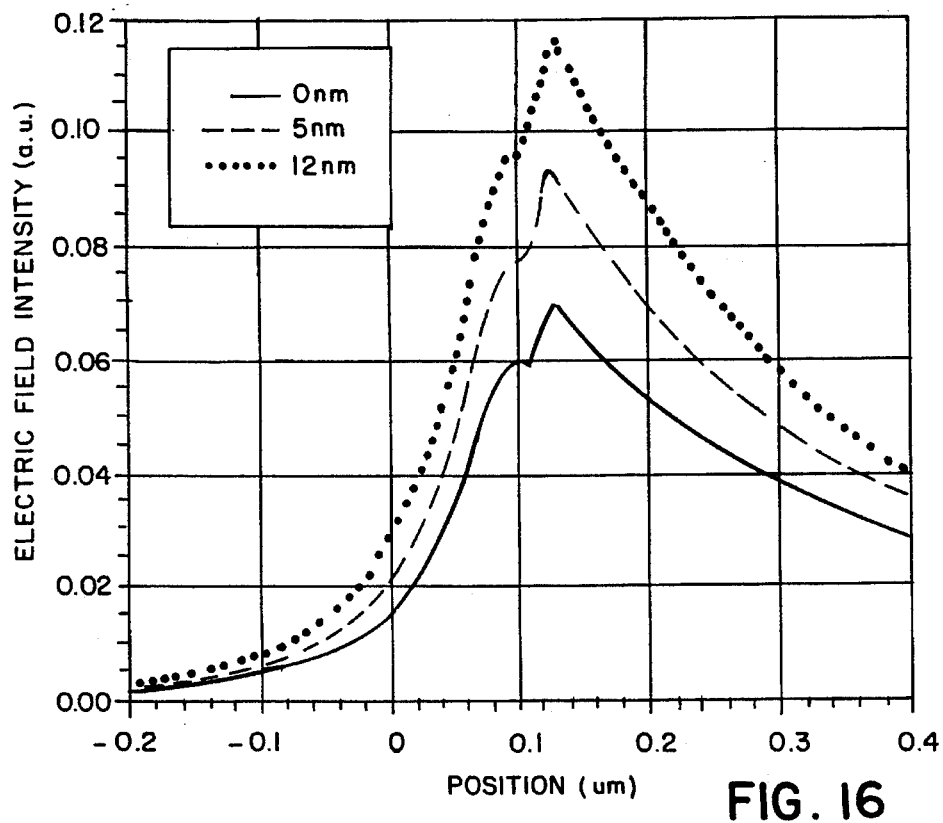
FIG. 16 graphically illustrates electric field intensity as a function of position for the sensor shown in FIG. 13 between −0.2 um and 0.4 um.

FIG. 13 shows a preferred embodiment of the sensor 1 of the present invention. The sensor apparatus includes a waveguide 103 having a low refractive index substrate 105 and a high refractive index layer 107 positioned on top of the substrate 105. A first low refractive index buffer layer 109 is positioned on the waveguide 103. A metallic layer 111 is positioned on the first buffer layer 109. A high refractive index tuning layer 113 is positioned on the metallic layer 111. A second low refractive index buffer layer 115 is positioned on the tuning layer 113. A light source 117 propagates light through the waveguide 103. A detector 119 monitors output signals 121 from the waveguide 103. Preferably, the high refractive index layer 113 is made of a high refractive index material such as tantalum pentoxide, titanium dioxide and zinc oxide. In one embodiment, the first low refractive index buffer layer 109 is approximately 1 micron thick, the metallic layer 111 is approximately 25 nm thick, the high refractive index tuning layer 113 is approximately 50 nm thick and the second low refractive index buffer layer 115 is approximately 50 nm thick. FIG. 14 graphically illustrates extinction ratio as a function of wavelength for several different metal layer thicknesses for the sensor shown in FIG. 13. FIG. 15 graphically illustrates electric field intensity as a function of position for the sensor shown in FIG. 13. FIG. 16 graphically illustrates electric field intensity as a function of position for the sensor shown in FIG. 13 between −0.2 um and 0.4 um.

Figure 18:
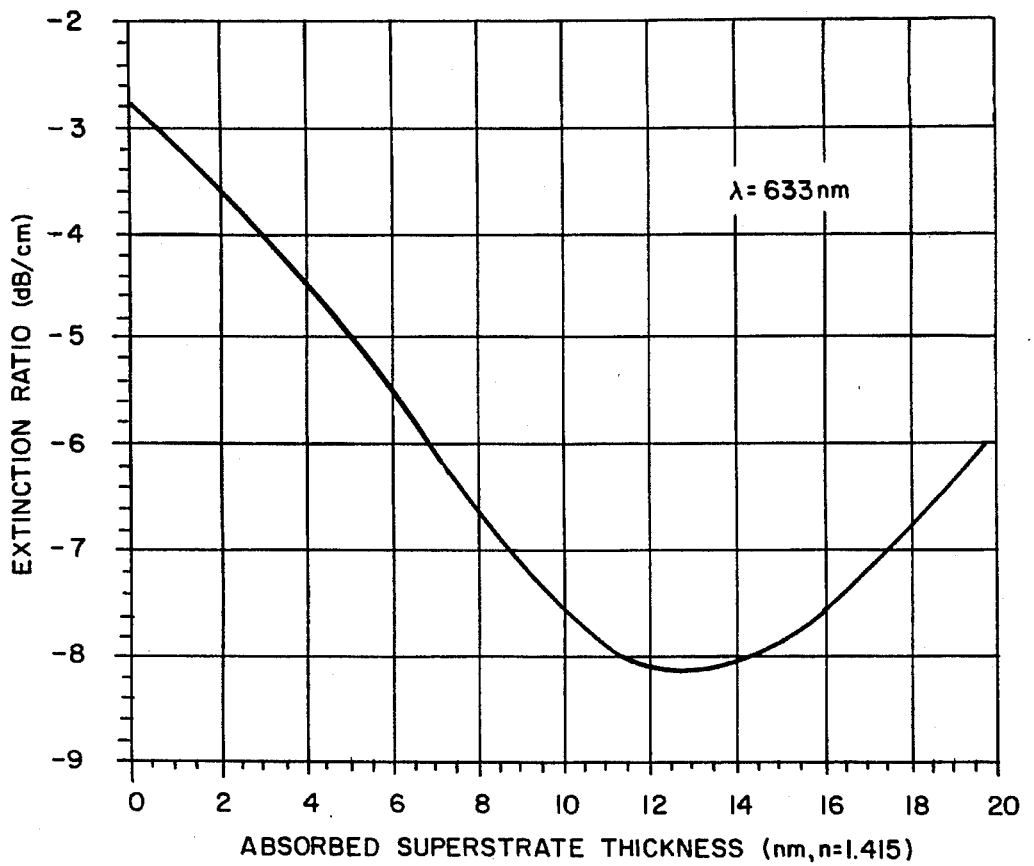
FIG. 18 graphically illustrates extinction ratio versus adsorbed superstrate thickness where the superstrate refractive index is assumed to be 1.415 for the sensor shown in FIG. 17.
Figure 17:
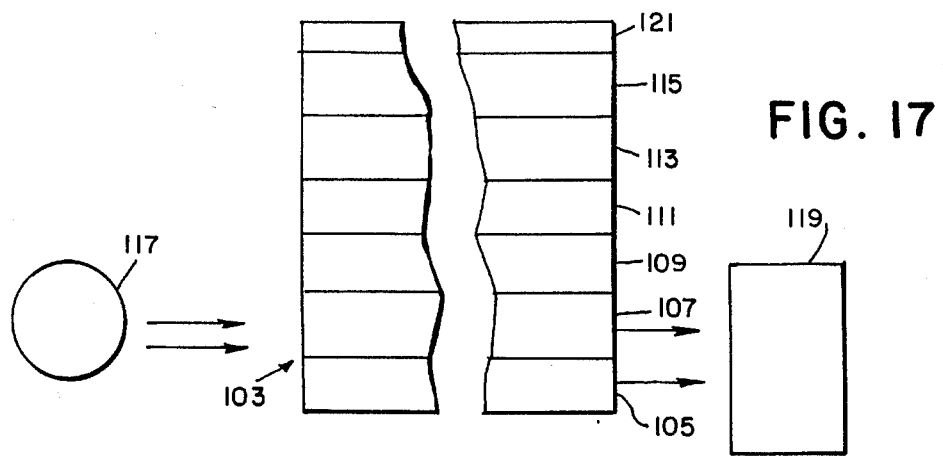
FIG. 17 is a schematic side view of an embodiment of the present invention having a light source, a detector and a surface plasmon resonance waveguide sensor. The sensor includes an optical waveguide structure, a first buffer layer, a tuning layer, a metal layer, a second buffer layer and a thin upper layer.
Figure 19:
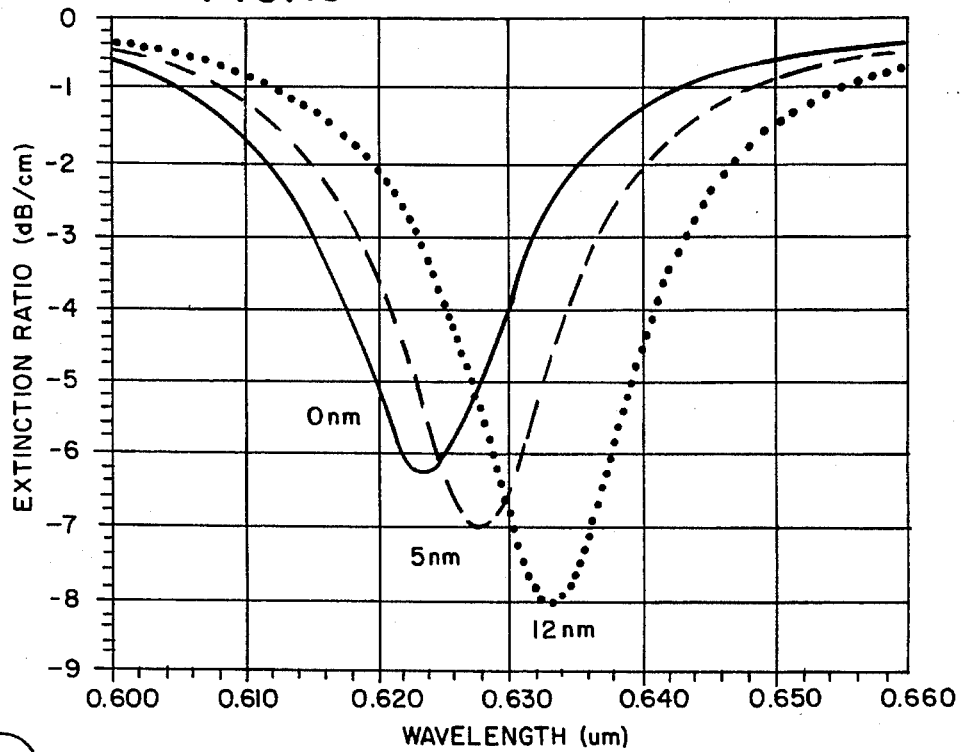
FIG. 19 graphically illustrates extinction ratio as a function of wavelength for several different metal layer thicknesses for the sensor shown in FIG. 17.

FIG. 17 shows another embodiment of the sensor 1 having a thin layer 121 positioned on the second low refractive index buffer layer 115. In preferred embodiments the thin layer 121 is an immunochemical sensor layer, a receptor layer, a glycoconjugate material layer or an affinity layer. FIG. 18 graphically illustrates extinction ratio versus adsorbed superstrate thickness where the superstrate refractive index is assumed to be 1.415 for the sensor shown in FIG. 17. FIG. 19 graphically illustrates extinction ratio as a function of wavelength for several different metal layer thicknesses for the sensor shown in FIG. 17.

The present invention can be configured with multiple optical waveguides such that multiple analytes can be evaluated simultaneously. In one embodiment, the sensor includes arrays of optical waveguide structures, each waveguide structure including a waveguide having a low refractive index substrate and a high refractive index layer positioned on top of the substrate, a first low refractive index buffer layer positioned on the waveguide, a metallic layer positioned on the first buffer layer, a high refractive index tuning layer positioned on the metallic layer, and a second low refractive index buffer layer positioned on the tuning layer, at least one light source for propagating light signals through the waveguide, and at least one detector for monitoring output signals from the waveguide. In another embodiment, the sensor includes multiple waveguide structures, each waveguide structure further comprising a waveguide having a low refractive index substrate and a high refractive index material deposited on the substrate, a low refractive index buffer layer positioned on the waveguide, a high refractive index tuning layer positioned on the buffer layer, and a metallic layer positioned on the tuning layer, at least one light source for propagating light signals through the waveguide, and at least one detector for monitoring output signals from the waveguide.

Figure 20:
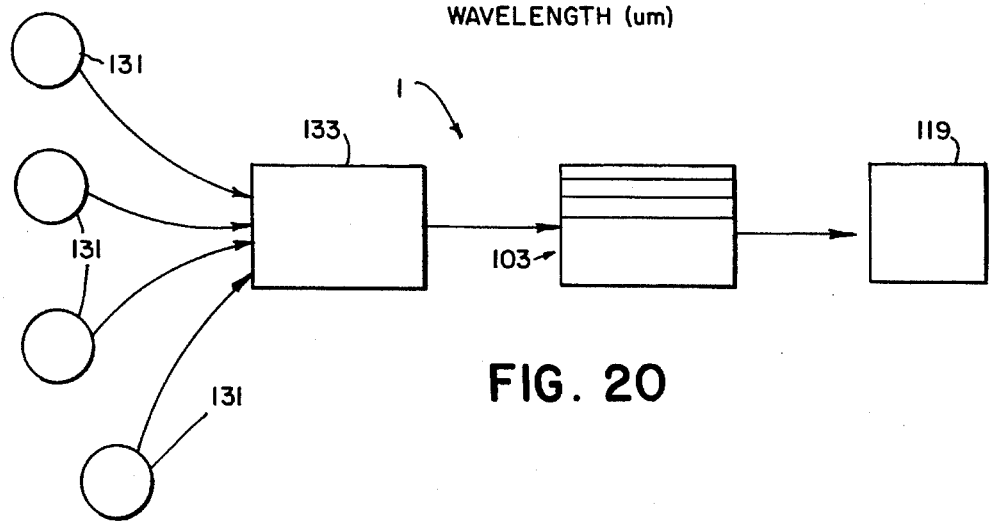
FIG. 20 schematically illustrates an embodiment of the present invention having multiple light sources, a Y branch, a sensor and a detector.

FIG. 20 shows another embodiment of the present invention having multiple light sources 131, such as lasers, as the light source. A Y branch 133 is positioned between the light sources 131 and the waveguide 103 of the sensor 1. That configuration allows the extinction ratio to be measured and provides an accurate measure of instrument response.

While the invention has been described with reference to specific embodiments, modifications and variations of the invention may be constructed without departing from the scope of the invention, which is defined in the following claims.

We claim:

1. A surface plasmon sensor apparatus comprising a waveguide, the waveguide having a low refractive index substrate and a high refractive index material deposited on the substrate, a low refractive index buffer layer positioned on the waveguide, a high refractive index tuning layer positioned on the buffer layer, a metallic layer positioned on the tuning layer, a light source for propagating light signals through the waveguide, and a detector for monitoring output signals from the waveguide.

2. The apparatus of claim 1, wherein the low refractive index substrate is a substrate selected from the group consisting of soda-lime glass, silicon dioxide, sol gel glass and BK-7 glass.

3. The apparatus of claim 2, wherein the high refractive index material is selected from the group consisting of ion-exchanged potassium in soda-lime glass, BK-7 glass, polyimide, titanium dioxide, tantalum pentoxide, silicon nitride, diamond and alumina.

4. The apparatus of claim 1, wherein the low refractive index substrate is selected from the group consisting of a silica sol-gel substrate and a fused silica substrate, and wherein the high refractive index material deposited on the substrate is poly(methyl methacrylate).

5. The apparatus of claim 1, wherein the low refractive index substrate is a BK-7 glass substrate, wherein the high refractive index layer formed on the substrate is potassium ion-exchanged glass, wherein the low refractive index buffer layer is a silicon dioxide layer, wherein the high refractive index tuning layer is an aluminum oxide, titanium or tantalum pentoxide layer, and wherein the metal layer is a gold layer.

6. The apparatus of claim 1, further comprising a thin layer positioned over the metal layer.

7. The apparatus of claim 6, wherein the thin layer is selected from the group consisting of an immunochemical probe phthalocyanine layer, a bioreceptor material layer and a polymer/dye layer.

8. The apparatus of claim 1, wherein the low refractive index substrate is a BK-7 glass substrate, wherein the high refractive index material deposited on the substrate is ion-exchanged potassium BK-7 glass, wherein the low refractive index buffer layer is a silicon dioxide layer, wherein the high refractive index tuning layer is selected from the group consisting of a titanium dioxide layer, a tantalum pentoxide layer and a silicon nitride layer, and wherein the metal layer is a gold layer.

9. The apparatus of claim 1, wherein the detector comprises a polarization beam splitter selected from the group consisting of a bulk polarization beam splitter and an integrated optical polarization beam splitter.

10. The apparatus of claim 9, wherein the output signals are a TE polarized signal and a TM polarized signal, and wherein the detector further comprises a first photodiode for receiving the TE polarized signal and for generating a first photodiode signal, a second photodiode for receiving the TM polarized signal and for generating a second photodiode signal, and a lock-in amplifier for receiving the first and second photodiode signals and for generating a difference signal.

11. The apparatus of claim 1, wherein the detector comprises a modulator for modulating the output signals, and wherein the modulator is selected from the group consisting of a vibrating mirror, an electro-optic modulator and a Mach-Zehnder interferometer.

12. The apparatus of claim 11, wherein the output signals are a TE polarized signal and a TM polarized signal, and wherein the detector further comprises a first photodiode for receiving the TE polarized signal and for generating a first photodiode signal, a second photodiode for receiving the TM polarized signal and for generating a second photodiode signal, and a lock-in amplifier for receiving the first and second photodiode signals and for generating a difference signal.

13. The apparatus of claim 1, further comprising an antibody coupled to the metal layer.

14. The apparatus of claim 1, wherein the metal layer is a gold layer modified by a carboxylated dextran for adsorbing microorganisms.

15. The apparatus of claim 1, further comprising a glycoconjugate material coupled to the metal layer.

16. The apparatus of claim 1, further comprising a thin nafion fluoropolymer layer positioned on the metal layer.

17. The apparatus of claim 1, wherein the light source is multiple light sources, and further comprising a Y branch positioned between the light sources and the waveguide.

18. A method for sensing by monitoring refractive indices and thicknesses of adsorbed films comprising the steps of assembling a structure having an optical waveguide, a low refractive index buffer layer on the waveguide, a high refractive index tuning layer on the buffer layer and a metal layer on the tuning layer, adsorbing a film on the metal layer, propagating light through the optical waveguide, detecting a TE polarization intensity and a TM polarization intensity, monitoring a ratio of TE and TM polarization intensities, and evaluating the ratio.

19. The method of claim 18, wherein detecting and monitoring further comprises feeding the TE polarization intensity to a first photodiode, feeding a TM polarization intensity to a second photodiode, generating a first signal from the first photodiode, generating a second signal from the second photodiode, routing the first and second signals to a lock-in amplifier, and generating a difference signal from the amplifier, and wherein evaluating the ratio further comprises normalizing the difference signal by division of the TE polarization intensity.

20. A detection system for detecting agents in an environment in a vicinity of a sensor comprising a light source for generating a light signal, a chopper for interrupting the light signal and for delivering an interrupted light signal, a surface plasmon waveguide sensor, an optical fiber extending between the chopper and the sensor for delivering the interrupted signal from the chopper to the sensor, a polarizer for receiving output signals from the sensor and for emitting polarized signals, and a photodetector for receiving the polarized signals, for monitoring the polarized signals and for determining characteristics of the environment in the vicinity of the sensor.

21. A surface plasmon sensor apparatus comprising a waveguide, the waveguide having a low refractive index substrate and a high refractive index layer positioned on top of the substrate, a first low refractive index buffer layer positioned on the waveguide, a metallic layer positioned on the first buffer layer, a high refractive index tuning layer positioned on the metallic layer, a second low refractive index buffer layer positioned on the tuning layer, a light source for propagating light signals through the waveguide, and a detector for monitoring output signals from the waveguide.

22. The apparatus of claim 21, wherein the high refractive index layer is made of a high refractive index material selected from the group consisting of tantalum pentoxide, titanium dioxide and zinc oxide.

23. The apparatus of claim 21, wherein the first low refractive index buffer layer is approximately 1 micron thick, the metallic layer is approximately 25 nm thick, the high refractive index tuning layer is approximately 50 nm thick and the second low refractive index buffer layer is approximately 50 nm thick.

24. The apparatus of claim 21, further comprising a thin layer positioned on the second low refractive index buffer layer.

25. The apparatus of claim 24, wherein the thin layer is selected from the group consisting of an immunochemical sensor layer, a receptor layer, a glycoconjugate material layer and an affinity layer.

26. A surface plasmon sensor apparatus comprising an array of optical waveguide structures, each waveguide structure further comprising a waveguide having a low refractive index substrate and a high refractive index layer positioned on top of the substrate, a first low refractive index buffer layer positioned on the waveguide, a metallic layer positioned on the first buffer layer, a high refractive index tuning layer positioned on the metallic layer, and a second low refractive index buffer layer positioned on the tuning layer, at least one light source for propagating light signals through the waveguide, and at least one detector for monitoring output signals from the waveguide.

27. A surface plasmon sensor apparatus comprising multiple waveguide structures, each waveguide structure further comprising a waveguide having a low refractive index substrate and a high refractive index material deposited on the substrate, a low refractive index buffer layer positioned on the waveguide, a high refractive index tuning layer positioned on the buffer layer, and a metallic layer positioned on the tuning layer, at least one light source for propagating light signals through the waveguide, and at least one detector for monitoring output signals from the waveguide.

28. A surface plasmon sensor apparatus comprising an optical waveguide, the waveguide having a low refractive index substrate and a high refractive index material deposited on the substrate, at least one low refractive index buffer layer positioned on the waveguide, at least one high refractive index tuning layer positioned above the buffer layers, a metallic layer positioned over the tuning layer layers, and a light source for propagating light signals through the waveguide, and a detector for monitoring output signals from the waveguide.

* * * * *